United States Patent [19]
Morelli et al.

[11] Patent Number: 6,087,322
[45] Date of Patent: *Jul. 11, 2000

[54] FRAGRANCE PRO-ACCORDS

[75] Inventors: Joseph Paul Morelli; Scott William Waite, both of Cincinnati; Stacy Renee Hertenstein, Mason; Kyle David Jones, West Chester, all of Ohio

[73] Assignee: The Procter & Gamble Company, Cincinnati, Ohio

[*] Notice: This patent is subject to a terminal disclaimer.

[21] Appl. No.: 09/033,496

[22] Filed: Mar. 2, 1998

Related U.S. Application Data

[63] Continuation-in-part of application No. 09/028,698, Feb. 24, 1998.
[60] Provisional application No. 60/044,562, Apr. 24, 1997.

[51] Int. Cl.⁷ .............................. A61K 7/46; A61K 6/00
[52] U.S. Cl. ................. 512/25; 512/26; 512/27; 512/1; 512/2; 424/401
[58] Field of Search .................. 512/2, 27, 25, 512/26; 424/401

[56] References Cited

U.S. PATENT DOCUMENTS

| | | | |
|---|---|---|---|
| 3,779,932 | 12/1973 | Jaggers | 252/108 |
| 3,849,326 | 11/1974 | Jaggers | 252/89 |
| 4,524,018 | 6/1985 | Yemoto | 252/522 |
| 4,994,266 | 2/1991 | Wells | 424/76.7 |
| 5,081,111 | 1/1992 | Akimoto | 525/285 |
| 5,266,592 | 11/1993 | Grub | 514/452 |
| 5,378,468 | 1/1995 | Suffis et al. | 424/401 |
| 5,626,852 | 5/1997 | Suffis | 424/401 |
| 5,648,328 | 7/1997 | Angell et al. | 510/441 |
| 5,656,584 | 8/1997 | Angell et al. | 510/441 |
| 5,773,402 | 6/1998 | D'Orazio | 510/380 |
| 5,814,590 | 9/1998 | Sherry et al. | 510/237 |
| 5,834,412 | 11/1998 | Rohrbaugh et al. | 510/324 |
| 5,858,948 | 1/1999 | Ghosh et al. | 510/300 |
| 5,858,959 | 1/1999 | Surutzidis et al. | 510/507 |

FOREIGN PATENT DOCUMENTS

| | | | |
|---|---|---|---|
| 738 700 A1 | 10/1996 | European Pat. Off. | C07C 43/303 |
| 786247 A1 | 7/1997 | European Pat. Off. | A61K 7/46 |
| 5-230496 | 9/1993 | Japan | C11B 9/00 |
| 7-179328 | 7/1995 | Japan | A61K 7/46 |
| 95/04809 | 2/1995 | WIPO | C11D 3/50 |
| 96/38528 | 12/1996 | WIPO | C11D 3/48 |

OTHER PUBLICATIONS

"Perfumes, Art, Science, & Technology", by P. M. Muler et al., Blackie Academic & Professional, (New York, 1994).
"Perfumery: Practice and Principles" Calkin, Rober R. and Jelline K,J. Stephan. pp. 238–239, 1994.

*Primary Examiner*—Gabrielle Brouillette
*Assistant Examiner*—Monique T. Cole
*Attorney, Agent, or Firm*—Richard S. Echler; Kim W. Zerby; Jacobus C. Rasser

[57] ABSTRACT

The present invention relates to perfume and fragrance pro-accords which are suitable for use in personal care and personal hygiene compositions as fragrance delivery systems. The pro-accords of the present invention slowly release fragrance raw materials upon contact with human skin thereby providing a prolonged fragrance benefit. The pro-accords serve as a means for delivering any fragrance raw material as well as other adjunct materials inter alia astringents, carriers, and diluents.

15 Claims, No Drawings

FRAGRANCE PRO-ACCORDS

This is a CIP of application Ser. No. 09/028,698, filed Feb. 24, 1998, pending.

This application claims benefit of Provisional Application No. 60/044,562.

FIELD OF THE INVENTION

The present invention relates to personal care and personal hygiene articles which comprise a fragrance delivery system comprising fragrance pro-accord compounds which are capable of releasing a mixture of fragrance raw materials in a sustained manner. The pro-accords of the present invention are suitable for use in delivering sustained release or enhanced longevity fragrances to a variety of personal care and personal hygiene products inter alia deodorants, body lotions or creams, and shampoos.

BACKGROUND OF THE INVENTION

Humans have applied scents and fragrances to their skin since antiquity. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modem chemistry, individual components responsible for the odor properties of these resins, gums and oils were isolated and subsequently characterized. Aside from common "perfume vehicles" inter alia, fine perfumes, colognes, eau de toilettes, and after-shave lotions, a wide variety of personal care or personal hygiene items also deliver for aesthetic reasons fragrance notes, accords, or fragrance "characteristics".

It is well known that mixtures of perfume or fragrance raw materials when deposited on the skin lose intensity and may change character with time, mainly due to factors such as differential evaporation and skin penetration. Many attempts have been made to minimize these drawbacks, but so far without notable success. Particularly, efforts have been made to prolong the diffusion, as well as to improve other characteristics of fragrance materials, by e.g. increasing the fragrance raw material concentration or by using additives such as silicones, glycerol, polyethylene glycols and so on. Such additions, however, have never been adequate to increase the longevity of the fragrance odor.

Accordingly, there remains a need in the art for a pro-accord which can be formulated into personal care and personal hygiene products wherein all components of a "perfume character" are released together producing a fragrance having enhanced longevity. Also, there is a need for a method for determining the composition of pro-accords which suitably deliver enhanced fragrance longevity when used in a personal care or personal hygiene composition.

BACKGROUND ART

In addition to the above-cited references, the following relate to the subject matter of fragrance ingredients. U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179, 328 published Jul. 18, 1995; JP 05-230496 published Sep. 7, 1993; WO 96/38528 published Dec. 5, 1996; WO 96/14827 published May 23, 1996; WO 95/04809 published Feb. 16, 1995; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that a perfume or fragrance accord can be released from one precursor pro-accord molecule. These pro-accords provide sustained perfume and fragrance retention when applied to human skin either directly or by way of a personal care or personal hygiene article. The personal care and personal hygiene articles include inter alia deodorants, body lotions or creams, ointments, balms, salves, antiseptics, suntan lotions, or shampoos. The pro-accords described herein comprise fragrances in a stable, releasable "pro-fragrance" form. The pro-accords can be formulated into any product which is deliverable to human skin, directly or indirectly, provided the product pH, carriers and adjunct materials are compatible with the pro-accord chemical form. Once in contact with human skin, the pro-accord is converted to the fragrance raw material mixture at a rate which provides extended fragrance benefits. The fragrance delivery systems of the present invention can be a mixture of any number of pro-accords and can cover any fragrance "characteristic" or desired fragrance volatility.

The first aspect of the present invention relates to compositions which are applied to skin, said compositions having increased fragrance retention and fragrance longevity. The suitable compositions of the present invention are inter alia deodorants, body lotions or creams, sun tan lotions, and shampoos, comprising:

a) at least about 0.01%, preferably from about 0.01% to about 10%, more preferably from about 0.1% to about 1% by weight, of a fragrance delivery system comprising one or more pro-accords, provided each pro-accord:
   i) comprises fragrance raw materials having a molecular weight greater than or equal to about 100 g/mol;
   ii) has a molecular weight greater than or equal to about 300 g/mol;
   iii) has a molecular weight at least two times greater than the lowest molecular weight fragrance raw material which comprises said pro-accord; and
   iv) has a fragrance release half-life greater than or equal to about 0.1 hours when measured in $NaH_2PO_4$ buffer at pH 5.3 and less than about 12 hours when measured in $NaH_2PO_4$ buffer at pH 2.5;

b) at least about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, and mixtures thereof; and c) the balance carriers.

A further aspect of the present invention is to provide personal care compositions comprising pro-accords which provide fragrance raw materials at a level wherein the "odor value" or "level of noticeability" is greater than or equal to 1 as defined herein.

It is another aspect of the present invention to provide a method for delivering an extended fragrance benefit to personal care articles. It is a further aspect of the present invention to provide a means of delivering a fragrance raw material containing perfume accord via a single pro-accord molecule. It is yet a further aspect of the present invention to provide pro-accord compounds which are formed from n fragrance raw materials but which deliver n+1 fragrance raw materials when hydrolyzed upon skin or other substrate. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

The compositions or the present invention can be suitably defined as comprising:

one or more fragrance pro-accords which provide extended fragrance benefits, provided said pro-accord:

a) has a molecular weight greater than or equal to 300 g/mol;

b) a fragrance release half life measured at pH 5.3 of from greater than or equal to 0.1 hours to less than or equal to 30 hours.

c) a skin performance index greater than or equal to 0.5.

The personal care compositions of the present invention comprise a fragrance delivery system which lays down one or more fragrance "pro-accord" compounds onto the skin, hair or other substrate during usage. Because the pro-accords of the present invention generally have a higher molecular weight than uncombined fragrance raw materials and other "pro-fragrance-type" compounds (i.e. pro-fragrances which only deliver a single equivalent of a fragrance raw material), they are a means for effectively delivering two or more fragrance raw materials in a manner which results in enhanced longevity of the fragrance raw materials on human skin or other substrate. Fragrance raw materials or pro-fragrance materials not within the scope of the present invention have been found to be too volatile to provide a sustained fragrance. Indeed, many "pro-fragrances" have been found to evaporate from the skin prior to hydrolysis and release of their fragrance material.

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds having a molecular weight of at least 100 g/mol and which are useful in imparting an odor, fragrance, essence, or scent either alone or in combination with other "fragrance raw materials".

Typically "fragrance raw materials" comprise inter alia alcohols, ketones, aldehydes, esters, ethers, nitrites, and cyclic and acyclic alkenes such as terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

For example, but not by way of limitation, the fragrance accords released by the pro-accords of the present invention have a "heart", "character", or "note" which is described as inter alia rose, jasmin, lilac, lily of the valley, violet, orange, peach, watermelon, and lemon. The accord may be further "modified" or "twisted" by the use of modifier top or middle notes which, as an additional benefit afforded by the present invention, can be incorporated into the pro-accord. For example, a "rose essence" may be combined with a "green" modifier to "shift the fragrance accord character".

The present invention also provides for pro-accords which are capable of releasing fragrance raw materials at a rate which is of utility to the formulator of fine fragrances or perfumes. For example, as described further herein below, the pro-accords of the present invention have a fragrance release half-life of greater than or equal to 0.1 hours at pH 5.3 and less than or equal to 12 hours at pH 2.5. In addition, the fragrance raw materials are released at a level wherein the odor value of said fragrance raw material is greater than 1.

Pro-Accords

The pro-accords of the present invention are comprised of one or more fragrance raw materials. The fragrance raw materials selected to comprise the final released accord are converted into a chemical species or reactive chemical form which releases the fragrance raw materials when the pro-accord is subjected to the proper conditions which trigger hydrolysis. Depending upon the particular embodiment chosen, the hydrolysis conditions may range from the acid mantle of human skin, to the nascent moisture which comprises air. The chemically modified forms of the fragrance raw materials in their releasable-form are the "pro-accords" of the present invention. One principle aspect of the present invention is the ability of pro-accords described herein to deliver more than one fragrance raw material when the "pro-accord" has been formed from only one fragrance raw material. All of the pro-accords of the present invention are capable of releasing at least two fragrance raw materials (hereinafter "binary accord") upon deposition, for example, onto skin or hair. There are two types of pro-accords; "symmetrical" pro-accords and "unsymmetrical" pro-accords each described herein further below.

Molecular Weight

The pro-accords of the present invention generally have a molecular weight of at least 300 g/mol, preferably greater than 325 g/mol, more preferably greater than 350 g/mol. It is also a condition of the present invention that the final molecular weight of the pro-accord is at least 2 times, preferably at least 2.25 times, more preferably 2.5 times, most preferably at least 2.75 times the molecular weight of the lowest fragrance material component.

For the purposes of the present invention, only fragrance raw materials having a molecular weight of at least 100 g/mol are considered "fragrance raw materials" according to the present invention. Therefore, low molecular weight materials inter alia methanol, ethanol, methyl acetate, ethyl acetate, and methyl formate which are common components of fragrance accords are excluded from the class of compounds defined herein as "fragrance raw materials". However, the formulator may wish to deliver these lower molecular weight materials (less than a molecular weight of 100 g/mol) as carriers, astringents, diluents, balancers, fixatives, or as other suitable adjunct materials.

By way of illustration and not limitation, the pro-accord tris(geranyl) orthoformate is considered, for the purposes of the present invention to be formed from three equivalents of geraniol. This pro-accord releases the binary accord geraniol/geranyl formate. This pro-accord has a molecular weight of approximately 472 g/mol. The lowest molecular weight fragrance raw material which is a component of tris(geranyl) orthoformate is geraniol which has a molecular weight of approximately 154 g/mol. Therefore tris(geranyl) orthofornate has a molecular weight greater than 3 times the molecular weight of the lowest molecular weight fragrance raw material component (geraniol) and hence is a most preferred pro-accord.

For the purposes of the present invention substituted or unsubstituted alkyleneoxy units are defined as moieties having the formula:

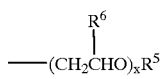

wherein $R^5$ is hydrogen, methyl, and mixtures thereof; $R^6$ is hydrogen, methyl, ethyl, and mixtures thereof; the index x is from 1 to about 20.

For the purposes of the present invention substituted or unsubstituted alkyleneoxyalkyl are defined as moieties having the formula:

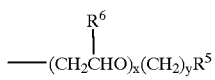

wherein $R^5$ is hydrogen, $C_1$–$C_{18}$ alkyl, $C_1$–$C_4$ alkoxy, and mixtures thereof; $R^6$ is hydrogen, methyl, ethyl, and mixtures thereof; the index x is from 1 to about 20 and the index y is from 2 to about 30.

For the purposes of the present invention substituted or unsubstituted alkylenearyl units are defined as moieties having the formula:

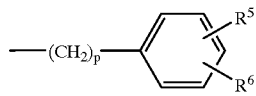

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof, p is from 1 to about 34.

For the purposes of the present invention substituted or unsubstituted aryloxy units are defined as moieties having the formula:

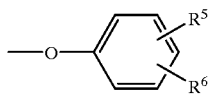

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof.

For the purposes of the present invention substituted or unsubstituted alkyleneoxyaryl units are defined as moieties having the formula:

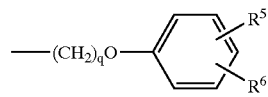

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof, q is from 1 to about 34.

For the purposes of the present invention substituted or unsubstituted oxyalkylenearyl units are defined as moieties having the formula:

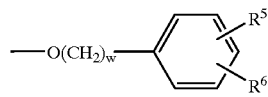

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof, w is from 1 to about 34.

Orthoesters

One class of preferred compounds useful as pro-accords according to the present invention are orthoesters having the formula:

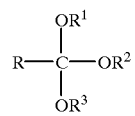

wherein hydrolysis of the orthoester releases fragrance raw material components according to the following scheme:

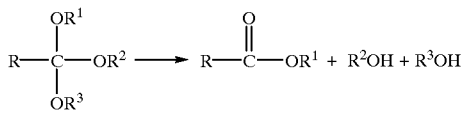

wherein R is hydrogen, $C_1$–$C_8$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof, preferably R is hydrogen, methyl, ethyl, and phenyl. $R^1$, $R^2$ and $R^3$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitrilo, halogen, nitro, carboxyl (—CHO; —$CO_2H$; —$CO_2R'$; —$CONH_2$;

—CONHR'; —CONR'$_2$; wherein R' is $C_1$–$C_{12}$ linear or branched alkyl), amino, $C_1$–$C_{12}$ mono- and dialkylamino, and mixtures thereof.

Non-limiting examples of $R^1$, $R^2$ and $R^3$ are methyl, 2,4-dimethyl-3-cyclo-hexene-1-methyl (Floralol), 2,4-dimethyl cyclohexane methyl (Dihydro floralol), 5,6-dimethyl-1-methylethenyl-bicyclo[2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-Δ$^2$-β-norbomanylethyl, 2-methyl-2-cyclohexylethyl, 1-(4-isopropylcyclohexyl) ethyl, 1-phenyl-1-hydroxyethyl, 1,1-dimethyl-2-phenylethyl, 1,1-dimethyl-2-(4-methylphenyl)ethyl, propyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl) propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene) butyl, 2-methyl-4-(2,2,3-trimethyl-3-cyclopenten-1-yl) butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo-[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-i -phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-1-(1-methylethyl)-3-cyclohexen-1-yl, 2-(5,6,6-trimethyl-2-norbomyl) cyclohexyl, isobomylcyclohexyl, 3,3,5-trimethylcyclohexyl, 1-methyl-4-isopropylcyclohex-3-yl (menthol), 1,2-dimethyl-3-(1-methylethyl)-cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4-heptadien-1-yl, 3,4,5,6,6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo-[2.2.1]hept-2-yl, 2,6-dimethylhept-2-yl, 2,6,6-trimethylbicyclo[1.3.3]hept-2-yl, octyl, 2-octenyl, 2-methyloctan- 2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa-5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7,11-trimethyl-2,6,10-dodecatrien- 1-yl (farnesyl), 3,7,11-trimethyl-1,6,10-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl, 2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)- 1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)-carboxy-1-hydroxyphenyl, 2-(ethyl) carboxy-1-hydroxyphenyl, 6-(methyl)carboxy-2,5-dimethyl-1,3-dihydroxyphenyl, 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4-hydroxybenzaldehyde, decahydro-2-naphthyl, 2,5,5-trimethyl-octahydro-2-naphthyl, 1,3,3-trimethyl-2-norbornyt (fenchyl), 3a,4,5,6,7,7a-hexahydro-2,4-dimethyl-4,7-methano-1H-inden-5-yl, 3a,4,5 ,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Also $R^1$, $R^2$, or $R^3$ units may serve to link two pro-accords for the purpose of providing greater substantivity. An example of pro-accord linking by a diol has the following formula:

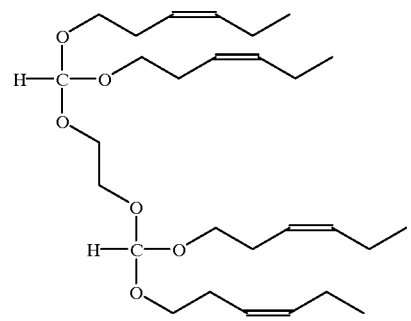

Orthoester Releasable Components: Hydrolysis of the orthoesters of the present invention have two types of releasable components, namely alcohols and esters. Hydrolysis of an orthoester will yield two equivalents of releasable alcohol, preferably a primary or secondary alcohol and one equivalent of releasable ester. The released ester, when taken together with the released alcohol, forms a binary fragrance accord. For example tri-geranyl orthoformate releases the binary accord geraniol/geranyl formate.

Preferred esters which are releasable components of the orthoesters of the present invention included but are not limited to geranyl formate, citronellyl formate, phenylethyl formate, phenoxyethyl formate, trans-2-hexenyl formate, cis-3-hexenyl formate, cis-6-nonenyl formate, 9-decenyl formate, 3,5,5-trimethylhexyl formate, 3-methyl-5-phenylpentanyl formate, 6-methylheptan-2-yl formate, 4-(2,2,6-trimethyl-2-cyclohexen-1-yl)-3-buten-2-yl formate, 3-methyl-5-(2,2,3-trimethyl-3-cyclopenten-1-yl)-4-penten-2-yl formate, menthyl formate, 4-isopropylcyclohexyleth-2-yl formate, 6,8-dimethylnonan-2-yl formate, decahydro-β-naphthyl formate, 4-isoproylcyclo-hexylmethyl formate, linalyl formate, lavandulyl formate, citronellyl formate, α-terpinyl formate, nopyl formate, isobornyl formate, bornyl formate, isobornyl formate, guaiyl formate, 2-tert-butylyclohexyl formate, 4-tert-butylcyclohexyl formate, decahydro-β-naphthyl formate, menthyl formate, p-menthanyl formate, neryl formate, cinnamyl formate, ethyl acetate, butyl acetate, isoamyl acetate, hexyl acetate, 3,5,5-trimethylhexyl acetate, geranyl acetate, citronellyl acetate, phenylethyl acetate, phenoxyethyl acetate, trans-2-hexenyl acetate, cis-3-hexenyl acetate, cis-6-nonenyl acetate, 9-decenyl acetate, 3-methyl-5-phenylpentanyl acetate, 6-methyl-heptan-2-yl acetate, 4-(2,2,6-trimethyl-2-cyclohexen-1-yl)-.3-buten-2-yl acetate, 3-methyl-5-(2,2,3-trimethyl-3-cyclopenten-1-yl)-4-penten-2-yl acetate, decahydro-β-naphthyl acetate, menthyl acetate, benzyl acetate, 4-isopropylcyclohexyleth-2-yl acetate, 6,8-dimethylnonan-2-yl acetate, 1-phenylethyl acetate, 4-isoproylcyclo-hexylmethyl acetate, linalyl acetate, lavandulyl acetate, citronellyl acetate, α-terpinyl acetate, nopyl acetate, isobornyl acetate, bornyl acetate, isobornyl acetate, guaiyl acetate, 2-tert-butylylcyclohexyl acetate, 4-tert-butylcyclohexyl acetate, decahydro-β-naphthyl acetate, menthyl acetate, p-menthanyl acetate, neryl acetate, cinnamyl acetate, ethyl propionate, ethyl butyrate, butyl butyrate, isoamyl butyrate, hexyl butyrate, cis-3-hexenyl butyrate, cis-3-hexenyl isobutyrate, ethyl isovalerate, 2-methylbutyrate, ethyl hexanoate, 2-propenyl hexanoate, ethyl heptanoate, 2-propenyl heptanoate, ethyl octanoate, ethyl 2-trans-4-cis-decadienoate, methyl 2-nonynoate, benzyl propionate, benzyl isovalerate, phenylethyl isobutyrate, phenylethyl isovalerate, α,α-dimethyl phenylethyl butyrate, methyl benzoate, hexyl benzoate, benzyl benzoate, ethyl phenylacetate, geranyl phenylacetate, 1-phenylethyl phenylacetate, methyl cinnamate, benzyl cinnamate, phenylethyl cinnamate, geranyl propionate, geranyl isobutyrate, geranyl isovalerate, linalyl propionate, linalyl buryrate, linalyl isobutyrate, citronellyl propionate, citronellyl isobutyrate, citronellyl isovalerate, citronellyl tiglate, allyl 3-cyclohexylpropionate, methyl dihydrojasmonate, methyl 2-hexyl-3-oxocyclopentane-carboxylate, and mixtures thereof.

Non-limiting examples of alcohols suitably released by the hydrolysis of the orthoester pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo [2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-$\Delta^2$-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, n-butanol, 2-butanol, 3-methylbutanol, 3-(4-methylcyclohex-3-ene) butanol, 2-methyl-4-(2,2,3-trimethyl-3-cyclopenten-1-yl) butanol, 2-ethyl-4-(2,2,3-trimethyl-cyclopent-3-enyl)-2-buten-1-ol, 3-methyl-2-buten-1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-( 4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0 (2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, I -methyl-4-isopropenylcyclohexan-3-ol, 4-iso-propyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1-methylethyl)-3-cyclohexen-1-ol, 2-(5,6,6-trimethyl-2-norbornyl) cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethy-3-hydroxy-2-methylenebicyclo[3.1.1] heptane, 1,7,7-trimethylbicyclo[2.2.1]heptan-2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadecl-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl- 1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, and mixtures thereof.

Preferred alcohols released by the orthoesters of the present invention are 4-(1-methylethyl) cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)-ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Non-limiting examples of orthoester pro-fragrances according to the present invention are tris(geranyl) orthoformate, tris(cis-3-hexen-1-yl) orthoformate, tris (phenylethyl) orthoformate, bis(citronellyl) ethyl orthoacetate, triscitronellyl orthoformate, tris(cis-6-nonenyl) orthoformate, tris(phenoxyethyl) orthoformate, tris (geranyl, neryl) orthoformate (70:30 geranyl:neryl), tris(9-decenyl) orthoformate, tris(3-methyl-5-phenylpentanyl) orthoformate, tris(6-methylheptan-2-yl) orthoformate, tris ([4-(2,2,6-trimethyl-2-cyclohexen-1-yl)-3-buten-2-yl] orthoformate, tris[3-methyl-5-(2,2,3-trimethyl-3-cyclopenten-1-yl)-4-penten-2-yl] orthoformate, tris (menthyl) orthoformate, tris(4-isopropylcyclohexylethyl-2-yl) orthoformate, tris(6,8-dimethylnonan-2-yl) orthoformate, tris(phenylethyl) orthoacetate, tris(cis-3-hexen-1-yl) orthoacetate, tris(cis-6-nonenyl) orthoacetate, tris(citronellyl) orthoacetate, bis(geranyl) benzyl orthoacetate, tris(geranyl) orthoacetate, tris(4-isopropylcyclohexylmethyl) orthoacetate, tris(benzyl) orthoacetate, tris(2,6-dimethyl-5-heptenyl) orthoacetate, bis (cis-3-hexen-1-yl) amyl orthoacetate, and neryl citronellyl ethyl orthobutyrate. Orthoester pro-accords can be used to deliver inter alia binary fragrance accords, fragrance accords having a "binary characteristic" accord component in combination with a modifier accord, and fragrance accords comprising astringents, fixatives, or diluents.

Acetals and ketals

Another class of compound useful as pro-accords according to the present invention are acetals and ketals having the formula:

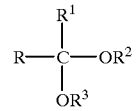

wherein hydrolysis of the acetal or ketal releases one equivalent of aldehyde or ketone and two equivalents of alcohol according to the following scheme:

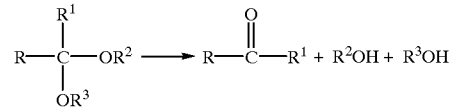

wherein R is $C_1$–$C_{20}$ linear alkyl, $C_3$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof. $R^1$ is hydrogen, R, or in the case wherein the pro-accord is a ketal, R and $R^1$ can be taken together to form a ring. $R^2$ and $R^3$ are independently selected from the group consisting of $C_1$–$C_{20}$ linear, branched, or substituted alkyl; $C_2$–$C_{20}$ linear, branched, or substituted alkenyl; $C_3$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, $C_1$–$C_{12}$ mono- and dialkylamino, and mixtures thereof.

Non-limiting examples of $R^2$ and $R^3$ include methyl, 2,4-dimethyl-3-cyclo-hexene-1-methyl (Floralol), 2,4- dimethyl cyclohexane methyl (Dihydro floralol), 5,6-dimethyl-1-methylethenyl-bicyclo [2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-Δ²-β-norbornanylethyl, 2-methyl-2-cyclohexylethyl, 1-(4-isopropylcyclohexyl) ethyl, 1-phenyl-1-hydroxyethyl, 1,1-dimethyl-2-phenylethyl, 1,1-dimethyl-2-(4-methylphenyl)ethyl, propyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl) propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene) butyl, 2-methyl-4-(2,2,3-trimethyl-3-cyclopenten-1-yl) butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo-[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-1-phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, ₄-isopropylcyclohexyl, 4-methyl-1-(1-methylethyl)-3-cyclohexen-1-yl, 2-(5,6,6-trimethyl-2-norbornyl) cyclohexyl, isobornylcyclohexyl, 3,3,5-trimethylcyclohexyl, 1-methyl-4-isopropylcyclohex-3-yl (menthol), 1,2-dimethyl-3-(1-methylethyl)-cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4-heptadien-1-yl, 3,4,5,6,6-pentamethyl-2-heptyl, 3,6-dimethyl-3-vinyl-5-hepten-2-yl, 6,6-dimethyl-3-hydroxy-2-methylenebicyclo[3.1.1]heptyl, 1,7,7-trimethylbicyclo-[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa-5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7,11-trimethyl-2,6,10-dodecatrien-1-yl (farnesyl), 3,7,11-trimethyl- 1,6,10,-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl, 2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)carboxy-1-hydroxyphenyl, 2-(ethyl) carboxy-1-hydroxyphenyl, 6-(methyl)carboxy-2,5-dimethyl-1,3-dihydroxyphenyl, 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4-hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl-4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Acetal Releasable Components: The acetals of the present invention have two types of releasable components, namely alcohols and aldehydes. Hydrolysis of an acetal will yield two equivalents of releasable alcohol and one equivalent of releasable aldehyde. The released aldehyde, when taken together with the released alcohol, forms a binary fragrance accord. For example bis(cis-3-hexenyl) vanillin acetal releases the binary accord vanillin/cis-3-hexenol.

When $R^1$ is hydrogen the pro-accords are capable of releasing an aldehyde component. Preferred aldehydes which are releasable components of the acetals of the present invention include but are not limited to phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal (Lilial), 3-(4-t-butylphenyl)propanal (Bourgeonal), 3-(4-methoxyphenyl)-2-methylpropanal (Canthoxal), 3-(4-isopropylphenyl)-2-methylpropanal (Cymal), 3-(3,4-methylenedioxyphenyl)-2-methylpropanal (Helional), 3-(4-ethylpheny)-2,2-dimethylpropanal (Floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (Melonal), 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10-trimethyl-9-undecenal (Adoxal), undec-10-enyl aldehyde, undec-8-enanal, dodecanal, tridecanal, tetradecanal, anisaldehyde, bourgenonal, cinnamic aldehyde, α-amylcinnam-aldehyde, α-hexyl cinnamaldehyde, methoxy-cinnamaldehyde, citronellal, hydroxy-citronellal, isocyclocitral, citronellyl oxyacetaldehyde, cortexaldehyde, cumminic aldehyde, cyclamen aldehyde, florhydral, heliotropin, hydrotropic aldehyde, lilial, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-carboxaldehyde (Lyral), 2,4-dimethyl-3-cyclohexene-1-carboxaldehyde (Triplal), 1-methyl-3-(4-methylpentyl)-3-cyclohexencarboxaldehyde (Vernaldehyde), p-methylphenoxyacetaldehyde (Xi aldehyde), and mixtures thereof.

More preferably the aldehydes released by the acetals of the present invention are 4-(4-hydroxy-4-methylpentyl)-3-cyclohexene-1-carboxaldehyde (lyral), phenylacetaldehyde, methylnonyl acetaldehyde, 2-phenylpropan-1-al (hydrotropaldehyde), 3-phenylprop-2-en-1-al (cinnamaldehyde), 3-phenyl-2-pentylprop-2-en-1-al (α-amylcinnamaldehyde), 3-phenyl-2-hexylprop-2-enal (α-hexylcinnamaldehyde), 3-(4-isopropylphenyl)-2-methylpropan-1-al (cyclamen aldehyde), 3-(4-ethylphenyl)-2,2-dimethylpropan-1-al (floralozone), 3-(4-tert-butylphenyl)-2-methylpropanal, 3-(3,4-methylenedioxyphenyl)-2-methylpropan-1-al (helional), 3-(4-ethylphenyl)-2,2-dimethylpropanal, 3-(3-isopropylphenyl)butan-1-al (flohydral), 2,6-dimethylhep-5-en-1-al (melonal), n-decanal, n-undecanal, n-dodecanal, 3,7-dimethyl-2,6-octadien-1-al (citral), 4-methoxybenzaldehyde (anisaldehyde), 3-methoxy-4-hydroxybenzaldehyde (vanillin), 3-ethoxy-4-hydroxybenzaldehyde (ethyl vanillin), 3,4-methylenedioxybenzaldehyde (heliotropin), 3,4-dimethoxybenzaldehyde Ketal Releasable Components: The ketals of the present invention have two types of releasable components, namely alcohols and ketones. Hydrolysis of a ketal will yield two equivalents of releasable alcohol and one equivalent of releasable ketone. The released ketone, when taken together with the released alcohol, forms a binary fragrance accord. For example bis(linalyl) β-ionone ketal releases the binary accord linalool/β-ionone.

When $R^1$ is a moiety as described herein above other than hydrogen, the pro-accords are capable of releasing an ketone component. Preferred ketones which are releasable components of the ketals of the present invention include but are not limited to α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl)butan-2-one, methyl, β-naphthyl ketone, methyl cedryl ketone, 6-acetyl-1,1,2,4,4,7-hexamethyltetralin (tonalid), 1-carvone, 5-cyclohexadecen-1-one, acetophenone, decatone, p-hydroxyphenylbutan-2-one, 2-[2-(4-methyl-3-cyclohexenyl-1-yl)propyl[cyclopentan-2-one, 2-sec-butylcyclohexanone, β-dihydro ionone, allyl ionone, α-irone, α-cetone, α-irisone, acetanisole, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, ethyl amyl ketone, ethyl pentyl ketone, menthone, methyl-7,3-dihydro-2H-1,5-benzodioxepine-3-one, fenchone, and mixtures thereof.

More preferably the ketones which are released by the ketals of the present invention are α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl)butan-2-one, methyl β-naphthyl ketone, methyl cedryl ketone, 6-acetyl-1,1,2,4,4,7-hexamethyltetralin (tonalid), 1-carvone, 5-cyclohexadecen-1-one, and mixture thereof.

Non-limiting examples of alcohols suitably released by the hydrolysis of the acetal and ketal pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-$\Delta^2$-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, n-butanol, 2-butanol, 3-methylbutanol, 3-(4-methylcyclohex-3-ene) butanol, 2-methyl-4-(2,2,3-trimethyl-3-cyclopenten-1-yl) butanol, 2-ethyl-4-(2,2,3-trimethyl-cyclopent-3-enyl)-2-buten-1-ol, 3-methyl-2-buten-1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl-4-isopropenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1-methylethyl)-3-cyclohexen-1- ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethy-3-hydroxy-2-methylenebicyclo[3.1.1]heptane, 1,7,7-trimethylbicyclo[2.2.1]heptan-2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetrahydrofuran, β-caryophyllene alcohol, and mixtures thereof.

Preferred alcohols which are released by the acetals and ketals of the present invention are 4-(1-methylethyl)cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Orthocarbonates

Another class of preferred compounds useful as pro-accords according to the present invention are orthocarbonates having the formula:

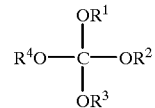

wherein hydrolysis of the orthoester releases the fragrance raw material components according to the following scheme:

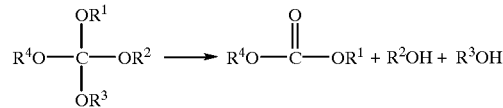

wherein $R^1$, $R^2$, $R^3$, and $R^4$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, $C_1$–$C_{12}$ mono- and dialkylamino, and mixtures thereof.

In addition to the initial release of two equivalents of alcohol and one equivalent of carbonate by the scheme depicted herein above, the carbonate pro-fragrances which are released by the orthocarbonates can continue to hydrolyze and further release two equivalents of one or more fragrance raw material alcohol according to the following scheme:

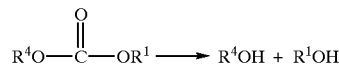

thereby providing up to four equivalents of fragrance raw material alcohol per equivalent of delivered orthocarbonate.

The carbonate pro-fragrance which is released by the orthocarbonate may itself be a fragrance raw material in addition to being a pro-fragrance, preferably the carbonate which is released serves as a fragrance raw material. An orthocarbonate which comprises four different fragrance raw materials will always release a carbonate that is a pro-accord (hydrolyzes to release a binary accord) in addition to any further fragrance properties attributable to the carbonate.

Non-limiting examples of $R^1$, $R^2$, $R^3$, and $R^4$ include methyl, 2,4-dimethyl-3-cyclo-hexene-1-methyl (Floralol), 2,4-dimethyl cyclohexane methyl (Dihydro floralol), 5,6-dimethyl-1-methylethenyl-bicyclo[2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), α-3,3-trimethyl-2-norboranylmethyl, 1,1-dimethyl-1-(4-methylcyclohex-3-enyl)methyl, ethyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-$\Delta^2$-β-norbomanylethyl, 2-methyl-2-cyclohexylethyl, 1-(4-isopropylcyclohexyl) ethyl, 1-phenyl-1-hydroxyethyl, 1,1-dimethyl-2-phenylethyl, 1,1-dimethyl-2-(4-methylphenyl)ethyl, propyl, 1-phenylpropyl, 3-phenylpropyl, 2-phenylpropyl (Hydrotropic Alcohol), 2-(cyclododecyl)-propan-1-yl (Hydroxyambran) 2,2-dimethyl-3-(3-methylphenyl)propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), α-n-pentyl-3-phenyl-2-propen-1-yl (α-amylcinnamyl alcohol), ethyl-3-hydroxy-3-phenyl propionate, 2-(4-methylphenyl)-2-propyl, butyl, 3-methylbutyl, 3-(4-methylcyclohex-3-ene)butyl, 2-methyl-4-(2,2,3-trimethyl-3-cyclopenten-1-yl)butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, pentyl, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo-[2.2.1.0(2,6)]hept-3-yl)-2-penten-1-yl (santalyl), 4-methyl-1-phenyl-2-pentyl, (1-methyl-bicyclo[2.1.1]hepten-2-yl)-2-methylpent-1-en-3-yl, 3-methyl-1-phenylpent-3-yl, 1,2-dimethyl-3-(1-methylethenyl)cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-i-(1-methylethyl)-3-cyclohexen-1-yl, 2-(5,6,6-trimethyl-2-norbornyl) cyclohexyl, isobornylcyclohexyl, 3,3,5-trimethylcyclohexyl, 1-methyl-4-isopropylcyclohex-3-yl (menthol), 1,2-dimethyl-3-(1-methylethyl)-cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4-heptadien-1-yl, 3,4,5,6,6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo-[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,0-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa- 5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7,11-trimethyl-2,6,10-dodecatrien-1-yl (farnesyl), 3,7,11-trimethyl-1,6,10,-dodecatrien-3-yl, 3,7,11,15-tetramethylhexadec-2-en-1-yl (phytyl), 3,7,11,15-tetramethylhexadec-1-en-3-yl (iso phytol), benzyl, p-methoxybenzyl (anisyl), para-cymen-7-yl (cuminyl), 4-methylbenzyl, 3,4-methylenedioxybenzyl,2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy- 1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy-4-(1-propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)carboxy-1-hydroxyphenyl, 2-(ethyl) carboxy-1-hydroxyphenyl, 6-(methyl)carboxy-2,5-dimethyl-1,3-dihydroxyphenyl, 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehyde, 2-ethoxy-4-hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl-4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, β-caryophyllenyl, and mixtures thereof.

Orthocarbonate Releasable Components: The initial hydrolysis of the orthocarbonates of the present invention release two types of components, alcohols and carbonates. As indicated herein above, the carbonates can further break down to release further alcohols. The first hydrolysis of an orthocarbonate pro-accord releases two equivalents of alcohol and one equivalent of carbonate. The released carbonate, when taken together with the released alcohol, forms a binary fragrance accord. For example tetrakis(geranyl) orthocarbonate releases the binary accord geraniol/bis (geranyl) carbonate. Non-limiting examples of alcohols suitably released by the hydrolysis of the orthocarbonate pro-accords include methanol, 2,4-dimethyl-3-cyclohexene-1-methanol (Floralol), 2,4-dimethyl cyclohexane methanol (Dihydro floralol), 5,6-dimethyl-1-methylethenylbicyclo

[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane methanol, 1,1-dimethyl-1-(4-methylcyclohex-3-enyl)methanol, ethanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-$\Delta^2$-β-norbomane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, $^2$-(4-methylphenyl)-2-propanol, n-butanol, 2-butanol, 3-methylbutanol, 3-(4-methylcyclohex-3-ene) butanol, 2-methyl-4-(2,2,3-trimethyl-3-cyclopenten-1-yl) butanol, 2-ethyl-4-(2,2,3-trimethyl-cyclopent-3-enyl)-2-buten- -ol, 3-methyl-2-buten- 1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol, 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethy-3-hydroxy-2-methylenebicyclo[3.1.1]heptane, 1,7,7-trimethylbicyclo[2.2.1]heptan-2-ol, 2,6-dimethylheptan-2-ol, 2,6,6-trimethylbicyclo[1.3.3]beptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydrozytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, and mixtures thereof.

Preferred alcohols released by the orthocarbonate proaccords of the present invention are 4-(1-methylethyl) cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl)phenol (isoeugenol), 2-methoxy-4-(2-propenyl)phenol (eugenol), 4-hydroxy-3-methoxybenzaldehyde (vanillin), and mixtures thereof.

Non-limiting examples of preferred orthocarbonate pro-accords according to the present invention include: bis (ethyl) bis(geranyl) orthocarbonate, bis(ethyl) bis (phenylethyl) orthocarbonate, bis(ethyl) bis(cis-3-hexenyl)

orthocarbonate, bis(ethyl) bis(citronellyl) orthocarbonate, bis(ethyl) bis(linalyl) orthocarbonate, bis(ethyl) bis (menthyl) orthocarbonate, bis(dodecyl) bis(geranyl) orthocarbonate, and bis(dodecyl) bis(phenylethyl) orthocarbonate.

The more preferred orthocarbonate pro-accords of the present invention comprise at least three of the $R^1$, $R^2$, $R^3$, and $R^4$ moieties which are derived from a fragrance raw material alcohol, thereby the preferred pro-fragrances have a molecular weight which is at least 3 times the molecular weight of the lowest "fragrance raw material alcohol" which comprises the orthocarbonate pro-fragrance. Further, the more preferred orthocarbonate pro-fragrances have a molecular weight which is greater than or equal to 325 g/mol.

Non-limiting examples of more preferred orthocarbonate pro-accords according to the present invention include: methyl tris(geranyl) orthocarbonate, methyl tris (phenylethyl) orthocarbonate, ethyl tris(phenylethyl) orthocarbonate, methyl tris(cis-3-hexenyl) orthocarbonate, ethyl tris(cis-3-hexenyl) orthocarbonate, methyl tris (citronellyl) orthocarbonate, ethyl tris(citronellyl) orthocarbonate, methyl tris(linalyl) orthocarbonate, ethyl tris(linalyl) orthocarbonate, methyl tris(menthyl) orthocarbonate, ethyl tris(menthyl) orthocarbonate, dodecyl tris(geranyl) orthocarbonate, and dodecyl tris(phenylethyl) orthocarbonate.

The most preferred orthocarbonate pro-accords of the present invention have each of the $R^1$, $R^2$, $R^3$, and $R^4$ moieties derived from a fragrance raw material alcohol, thereby the preferred pro-fragrances have a molecular weight which is at least 4 times the molecular weight of the lowest "fragrance raw material alcohol" which comprises the orthocarbonate pro-accord. Further, the preferred orthocarbonate pro-accords have a molecular weight which is greater than or equal to 350 g/mol.

Non-limiting examples of most preferred orthocarbonate pro-accords according to the present invention include: tetrakis(geranyl) orthocarbonate, tetrakis(phenylethyl) orthocarbonate, tetrakis(3-methyl-5-pentylpentyl) orthocarbonate, tetrakis(cis-3-hexenyl) orthocarbonate, bis (geranyl) bis(cis-3-hexenyl) orthocarbonate, bis (phenylethyl) bis(cis-3-hexenyl) orthocarbonate, tetrakis (citronellyl) orthocarbonate, tetrakis(linalyl) orthocarbonate, bis(linallyl) bis(geranyl) orthocarbonate, tetrakis(myrcenyl) orthocarbonate, tetrakis(cinnamyl) orthocarbonate.

Fragrance Release Half-life

The pro-accords useful in the personal care compositions of the present invention generally have a delayed release of final fragrance accord in order to achieve the increased fragrance longevity benefits described herein. However, the pro-accords generally also deliver the fragrance accords during a time period useful to the formulator, for example, within a time period desirable to the consumer.

For the purposes of the present invention the pro-accords generally have a "Fragrance Release Half-life" of less than or equal to 12 hours when measured in $NaH_2PO_4$ buffer at pH 2.5 and greater than or equal to 0.1 hour when measured in $NaH_2PO_4$ buffer at pH 5.3. The "Fragrance Release Half-life" is defined herein as follows.

Pro-accords deliver their corresponding mixture of fragrance raw materials or fragrance accords according to the equation:

$$\text{Pro-Accord} \rightarrow \text{Accord}$$

wherein the accord which is released may be a binary accord or a multiple fragrance raw material accord.

The rate at which the accord is released is defined by the formula:

$$\text{Rate} = k[\text{Pro-accord}]$$

and can be further expressed by the formula:

$$-\frac{d\,[\text{Pro-accord}]}{dt} = k[\text{Pro-accord}]$$

wherein k is the release rate constant and [Pro-accord] is the concentration of pro-accord. For the purposes of the present invention the "Fragrance Release Half-life", $t_{1/2}$, is related to the release rate constant by the formula:

$$t_{1/2} = \frac{0.693}{k}$$

and this relationship is used for the purposes of the present invention to determine the "fragrance Release Half-life" (FRHL).

Due to the hydrophobic nature of some pro-accords, it is necessary to conduct the determination of $t_{1/2}$ and k in a mixture of 90/10 dioxane/phosphate buffered water. The phosphate buffered water is prepared by admixing 3.95 mL of 85% phosphoric acid ($H_3PO_4$) and 24 g of sodium dihydrogen phosphate ($NaH_2PO_4$) with one liter of water. The pH of this solution is approximately 2.5. Next 10 mL of the phosphate buffer is admixed with 90 mL of dioxane and the pro-fragrance to be analyzed is added. The hydrolysis kinetics are then monitored by conventional HPLC at 30° C.

Table I lists several pro-accords according to the present invention with their corresponding $t_{1/2}$ values.

TABLE I

| Pro-accord | $t_{1/2}$* |
|---|---|
| tris(phenylethyl) orthoformate | 5.9 |
| tetrakis(phenylethyl) orthocarbonate | 4.8 |

*$t_{1/2}$ for the purposes of the present invention is measured in hours.

As indicated in the table above tris(phenylethyl) orthoformate is suitable for use as a pro-accord for delivering a "rose-floral" character note to an accord having enhance longevity. In some instances, it is desirable to formulate a fragrance delivery system having one or more pro-accords which deliver a rapid release of fragrance raw material in addition to the delayed onset of a fragrance. In such cases the hydrolysis rate, and therefore the determination of $t_{1/2}$ must be measured in a buffer system which can accommodate this more rapid hydrolysis rate. For example, the pro-fragrance tris(phenylethyl) orthoacetate is used to deliver a rapid onset of a "rose-floral" middle note by releasing the fragrance raw material phenylethyl alcohol. The relative release rate of this pro-accord can be suitably determined by substituting a phosphate buffer comprising 4.6 g of sodium dihydrogen phosphate ($NaH_2PO_4$) and 7.9 g of disodium hydrogen phosphate ($Na_2HPO_4$) admixed with 1 liter of water for the phosphate buffer described herein above.

Therefore, by admixing sufficient quantities of tris (phenylethyl) orthoformate and tris(phenylethyl) orthoacetate into a pro-accord the formulator can achieve a rapid as well as delayed onset of the "rose-floral" character note provided by the perfume raw material phenylethyl alcohol.

The pro-accords of the present invention are stable under pH conditions encountered in the formulation and storage of personal care and personal hygiene articles which have a pH of from about 7.1 to 11.5, and during solution-use of such products. Due to their high molecular weight and hydrophobicity, these pro-accord compounds remain deposited upon skin even when exposed to water (i.e. when formulated into a sun screen). Because the pro-accords are subject to hydrolysis when the pH is reduced, they hydrolyze to release their component fragrance compounds when applied to skin or are exposed even to reduced pH such as present in air and humidity. The reduction in pH should be at least 0.1, preferably at least about 0.5 units. Preferably the pH is reduced by at least 0.5 units to a pH of 7.5 or less, more preferably 6.9 or less. Preferably, the solution in which the pro-accord is applied is alkaline.

Odor Value

The pro-accords of the present invention typically have an Odor Value greater than or equal to about 1, preferably greater than or equal to about 5, more preferably greater than or equal to about 10. The term "Odor Value" is defined by the following formula:

$$OV = \frac{[\text{Concentration of } FRM]}{ODT}$$

wherein OV is the odor value of the fragrance raw material released upon the skin by the pro-accord. The odor value is the concentration of the fragrance raw material, FRM, on the skin surface divided by the Odor Detection Threshold, ODT. The term "level of noticeability" is often applied to and substituted for the term "odor value".

Odor Detection Threshold

For the purposes of the present invention the term "odor detection threshold" is defined as the level at which a fragrance raw material is perceptible to the average human. The odor detection threshold (ODT) of the compositions of the present invention are preferably measured by carefully controlled gas chromatograph (GC) conditions as described hereinbelow. The preferred fragrance raw materials of the present invention have an ODT of at least about 100 part per billion (ppb), more preferably 10 ppb, most preferably 1 ppb. Fragrance raw materials having an ODT greater than 10 parts per million (ppm) are typically avoided unless useful as an adjunct ingredient, for example, as an adjunct alcohol when adjusting the fragrance release half-life of an orthoester.

Determination of Odor Detection Thresholds is as follows. A gas chromatograph is characterized to determine the exact volume of material injected by a syringe, the precise split ratio, and the hydrocarbon response using a hydrocarbon standard of known concentration and chain-length distribution. The air flow rate in accurately measured and, assuming the duration of a human inhalation to last 0.02 minutes, the sampled volume is calculated. Since the precise concentration at the detector at any point in time is known, the mass per volume inhaled is known and hence the concentration of material. To determine whether a material has a threshold below 10 ppb, solutions are delivered to the sniff port at the back-calculated concentration. A panelist sniffs the GC effluent and identifies the retention time when odor is notice. The average over all panelists determines the threshold of noticeability or ODT. The necessary amount of analyte is injected onto the column to achieve a 10 ppb concentration at the detector. Typical gas chromatograph parameters for determining odor detection thresholds are listed below.

GC: 5890 Series II with FID detector 7673 Autosampler
Column: J&W Scientific DB-1, length 30 m, i.d. 0.25 mm, film thickness 1 µm.
Split Injection: 17/1 split ratio
Autosampler: 1.13 µl/injection
Column flow: 1.10 mL/min
Air flow: 345 mL/min
Inlet temperature: 245° C.
Detector temperature: 285° C.
Temperature Information:
  Initial temperature: 50° C.
  Rate: 5° C./min
  Final temperature: 280° C.
  Final time: 6 min Leading assumptions: 0.02 minutes per sniff and that GC air adds to sample dilution.

Skin Performance Index

Although a pro-accord may comprise a fragrance release half-life which ensures delivery of a fragrance accord during a period of time useful to the formulator, unless the fragrance raw materials which comprise said accord have ODT values small enough to be perceived by the user, the formulator will be compelled to use an inordinate amount of material to achieve a suitable fragrance level.

The pro-accords of the present invention have a Skin Performance Index (SPI) greater than or equal to 0.1, preferably greater than or equal to 0.5. The Skin Performance Index is defined by the following:

$$SPI = \frac{[\text{Odor Value}]^*}{t_{1/2}}$$

wherein the term [Odor Value]* is the estimated headspace concentration of a 1% solution of the fragrance raw material in ethanol divided by the odor detection threshold of the material, and $t_{1/2}$ is the fragrance release half-life measured at pH 5.3 in the above described buffer. For the purposes of the present invention, the $t_{1/2}$ of the SPI is measured at 5.3 and the value of the fragrance release half-life is preferably from 0.1 hours to 60 hours.

The estimated headspace concentration* of the fragrance raw material are found by using empirically determined KOVATS indices. "The Vapor Pressures of Pure Substances", T. Boublik et al., Elseiver, New York (1973) incorporated herein by reference, describes an index line for normal alkanes wherein a 1% solution of $C_{10}$ is equal to 30,000 ppb, a 1% solution of $C_{12}$ is equal to 3,000 ppb, a 1% solution of $C_{14}$ is equal to 300 ppb, a 1% solution of $C_{16}$ is equal to 30 ppb, etc. Using a series of n-alkanes as reference standards, the KOVATS index of a fragrance raw material is obtained from gas chromatographic analysis of the FRM. The Kovats index is then used to determine the relative vapor pressure and hence the head space concentration of the fragrance raw material.

"New Method for Estimating Vapor Pressure by the Use of Gas Chromatography" *J Chromatography A,* 79 p 123–129, (1996) and "Simple and Versatile Injection System for Capillary Gas Chromatographic Columns: Performance Evaluation of a System Including Mass Spectrometric and Light Pipe Fourier-Transform Infrared Detection", *J Chromatography A,* 713, p 201–215, (1996) included herein by reference, further describe methods and techniques suitable for use in determining the vapor pressure and head space concentration of FRM's as they relate to the term [Odor Value]* of the present invention.

Symmetrical Pro-accords

Symmetrical pro-accords release the same fragrance raw materials regardless of hydrolysis pathway. An example of a symmetrical pro-accord is tris(phenylethyl) orthoacetate which releases a binary accord having a "rose" characteristic comprising 2 parts phenylethyl alcohol and 1 part phenylethyl acetate according to the following scheme:

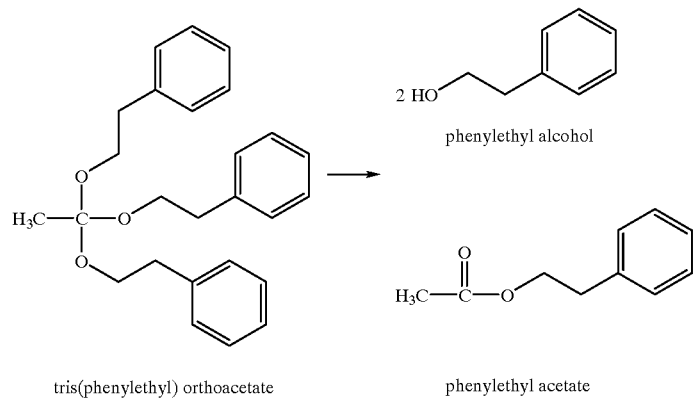

tris(phenylethyl) orthoacetate            phenylethyl alcohol phenylethyl acetate The phenylethyl alcohol/phenylethyl acetate (2:1) simple accord is useful in delivering to skin, hair or other substrate a rose or rose/floral characteristic. These are the only fragrance raw materials which are releasable by the pro-accord regardless of hydrolysis pathway.

"adjunct pro-accords" useful for releasing low molecular weight modifiers or astringents in addition to fragrance raw materials.

An example of an unsymmetrical pro-accord is bis (citronellyl) benzyl acetate capable of releasing the binary fragrance accord of citronellol/citronellyl acetate having a "rose" characteristic together with the benzyl alcohol/benzyl acetate "jasmin" modifiers according to the following scheme:

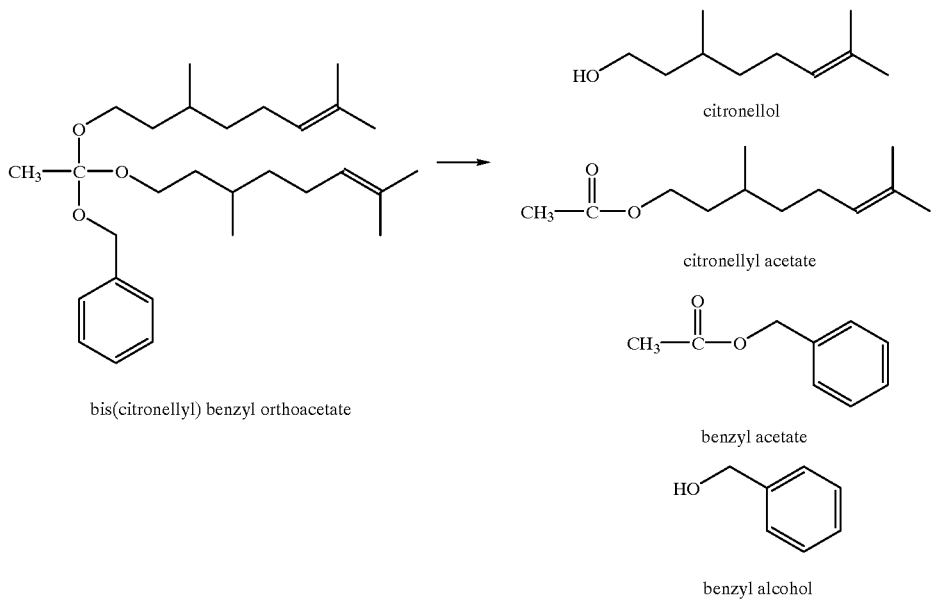

bis(citronellyl) benzyl orthoacetate citronellol citronellyl acetate benzyl acetate benzyl alcohol Unsymmetrical Pro-accords Unsymmetrical pro-accords have the capacity to release fragrance accords more complex than the binary fragrance accords released by symmetrical pro-accords. The composition of the released accord depends on the route of pro-accord hydrolysis. An unsymmetrical pro-accord can be designed by the formulator to release different ratios of fragrance raw materials based not only on the composition of the pro-accord but on the reactivity as well. In addition, unsymmetrical pro-accords can also be used to produce The above accord can be suitably modified by the formulator to adjust the relative proportions of the accord ingredients. For example, more of the "sweet" diluent benzyl alcohol can be delivered by adjusting the proportion of citronellol and benzyl alcohol used in the pro-accord. Bis (benzyl) citronellyl orthoacetate delivers the same fragrance raw materials as bis(citronellyl) benzyl orthoacetate, only the relative amounts of the released materials differ.

Increased Release Pro-accords

As described herein above, a principle aspect of the present invention is the ability of certain fragrance pro-accords, for example, orthoesters and orthocarbonates, to deliver n+1 fragrance raw materials when the "pro-accord"

has been formed from n fragrance raw materials. These "Increased Release" pro-accords are preferably formate, acetate, propionate, and benzoate orthoesters. Any fragrance raw material may be used to form the "increased release" pro-accord provided the final pro-accord:

a) has a molecular weight greater than or equal to about 300 g/mol;
b) has a molecular weight at least two times greater than the lowest molecular weight fragrance raw material which comprises said pro-accord; and
c) has a fragrance release half-life greater than or equal to about 0.1 hours when measured in $NaH_2PO_4$ buffer at pH 5.3 and less than about 12 hours when measured in $NaH_2PO_4$ buffer at pH 2.5.

The value of the index n is an integer from 1 to 3.

When present the "increased release" pro-accords comprise at least 0.01% of the increased fragrance retention composition, preferably at least about 0.1% more preferably at least about 0.5% by weight, of said composition. More than one "increased release" pro-accords may be combined together as described herein above to provide a complex perfume mixture or accord.

Examples of "increased release" pro-accords which are comprised of a single fragrance raw materials but which release at least 2 fragrance raw materials include but are not limited to tris(citronellyl) orthoformate which releases the binary accord citronellyl formate/citronellol; tris(citronellyl) orthoacetate which releases the binary accord citronellol/citronellyl acetate; tris(geranyl) orthoformate which releases the binary accord geraniol/geranyl formate; tris(geranyl) orthoacetate which releases the binary accord geraniol/geranyl acetate; tris(phenylethyl) orthoformate which releases the binary accord 2-phenylethanol/phenylethyl formate; tris(phenylethyl) orthoacetate which releases the binary accord 2-phenylethanol/phenylethyl acetate; tris(9-decenyl) orthoformate which releases the binary accord 9-decen-1-ol/9-decenyl formate; and tris(9-decenyl) orthoacetate which releases the binary accord 9-decen-1-ol/9-decenyl acetate.

The present invention also relates to a process for preparing unsymmetrical orthoester pro-accords comprising the step of admixing two or more fragrance raw material alcohols with an orthoester transesterifying agent. The transesterification may include the reaction of the alcohol mixture with agents such as tris methyl orthoformate. For example, the unsymmetrical orthoacetate geranyl neryl citronellyl acetate can be formed by the reaction of an admixture of geraniol nerol and citronellol with trimethyl orthoacetate under suitable conditions. The formulator may also adjust the proportions of the fragrance raw material alcohols in order to affect the balance of the releasable accord.

Skin Conditioning Lotions

An example of a skin care composition of the present invention comprises an ester having a total number of carbon atoms in excess of about 28, for example lauryl laurate, lauryl myristate, myristyl myristate, behenyl caprate, cetearyl palmitate, behenyl stearate, more preferably cetearyl palmitate and cetyl stearate.

The present compositions in addition to the esters described herein above, contain an emollient material in an amount such that the amount of ester plus emollient is from about 0.2% to about 25% of the total composition, preferably from about 4% to about 18%. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than 24 carbon atoms or branched and having more than 24 carbon atoms, if used as an emollient should preferably be used in an mount equal to about a third of the long chain ester. The particular emollient selected depends in part on the particular ester selected since proper plasticization, as indicated above, is desired. The emollient for the esters having more than 28 carbon atoms is preferably selected from the group consisting of squalane, liquid or solid paraffins and mixtures of fatty alcohols with squalane or paraffins. Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax. It is preferred that distilled water be used in the present compositions.

OPTIONAL COMPONENTS

Oil Phase Components

In addition to the long chain esters, emollients and emulsifiers described previously, the oil phase of the present compositions may contain a variety of materials including:

(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;

(b) Oils such as castor oil, jojoba oil, cottonseed oil, peanut oil and sesame oil;

(c) Waxes such as ceresin wax, carnuba wax, beeswax and castor wax;

(d) Lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference.

(e) Polyalkylenes such as hydrogenated polyisobutene and polyethylene; and (f) Sterols such as. cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase to the compositions may contain many different materials including:

(a) Humectants, such as sorbitol, glycerine, propylene glycol, alkoxylated glucose and hexanetriol at a level of from about 1% to about 20%.

(b) Thickening agents such as carboxyvinyl polymers, ethyl cellulose, polyvinyl alcohol, carboxymethyl cellulose, vegetable gums and clays such as Veegum-.RTM. (magnesium aluminum silicate, R. T. Vanderbilt, Inc.) at a level of from about 0.01% to about 6%;

(c) Proteins and polypeptides at a level of from about 0.1% to about 3%;

(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and (e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as dyes. The compositions of the present invention are preferably substantially free of materials which adversely affect their performance. Therefore, such things as polyethylene glycols are preferably present only at levels below about 1% of the total composition. The pH of the present compositions is preferably in the range of about 7.5–10.

METHOD OF MANUFACTURE

The compositions of the present invention generally have a lotion consistency and may be in the form of oil-in-water or water-in-oil emulsions with the former being preferred because of their more pleasing cosmetic properties. The compositions of the present invention are preferably made by the method comprising the steps of;

a) preparing the oil phase;

b) preparing the water phase; and c) adding the oil phase to the water phase.

Step (a) is carried out by heating the oil phase materials to a temperature of about 75° C. to about 100° C. Step (b) is carried out by heating the water phase materials to a temperature about the same as that of the oil phase. The emulsion is formed by slowly adding the oil phase prepared in step (a) to the water phase prepared in step (b) with stirring. The pro-accords which comprise the fragrance delivery system or other ingredients may be added to the phase in which they are soluble prior to the mixing of the two phases or added directly to the mixed water and oil phases.

In addition to the fragrance-containing compositions for use on human skin, the pro-accords of the present invention are also suitable for use in any odor controlling or fragrance mediating application. A example of this odor control capacity is animal litter and odor control articles useful in lining the cages, stalls, and other living areas of domesticated animals. For example, U.S. Pat. No. 5,339,769 Toth et al., issued Aug. 23, 1994 describes a process for making an absorbent composition which can well accommodate the pro-accord materials of the present invention.

An example of a suitable litter material which comprises the pro-accords of the present invention can be formed by the following process.

A Glatt fluid bed granulator is charged with 1,0000 g of bentonite clay (90% of the particles being greater than 420 microns) and 10 g of a cellulose ether (Methocel™ K15M Premium, a cellulose ether having a viscosity of 15,000 centipoise (cps) as a 2% aqueous solution). The granulator is started an the product temperature is brought up to about 40° C. (outlet temperature). When the outlet temperature reaches about 40° C., atomized water is sprayed onto the moving powders within the granulator. During the granulation process, inlet air temperature is maintained at 70° C. to 80° C.; air -atomization pressure is 28–35 psi; and the spraying cycle is for 45 seconds with a 15 second shaking time.

The clay/cellulose ether agglomerates swell over time. The water hydrates the cellulose ether polymer which produces adhesion to form the granule. At this time it is more advantageous to introduce the pro-accord materials and other aesthetic fragrances. The formation of the granule promotes aggregation of the small sized particles of the inert substrate, e.g. clay particles of about 50 to 600 microns. The formation of a granule significantly reduces the quality of dust in the final product while the litter forms an agglomerate when wetted.

In an alternative embodiment of the clay-based litter box articles/pro-accord admixture, once the clay particles have been formed, a concentrated solution, or an carrier alcohol-based admixture of the pro-accords may be delivered to the surface of the granule by a suitable means.

EXAMPLE 1

Preparation of tris(phenylethyl) orthoformate

To a 500 mL single neck flask assembled with a short path distillation head and a magnetic stirrer is combined phenylethyl alcohol (66 g), triethyl orthoformate (20.2 g) and 3 drops of concentrated sulfuric acid under a nitrogen atmosphere. The reaction mixture is heated for 3 hr at 100° C. to distill over ethanol. The reaction progress is monitored by the amount of ethanol generated and by silica gel thin layer chromatography (TLC) eluting with 4% ethyl acetate/petroleum ether and development with iodine stain. Upon completion, the reaction mixture is diluted with diethyl ether (200 mL) and the organic phase washed three times with saturated aqueous sodium carbonate. The organic phase is dried over magnesium sulfate, filtered, and the resulting clear solution is concentrated in vacuo. The product is purified by Kugelrohr distillation wherein the fraction in the range 120–140° C., at 0.1 mm Hg is collected to yield 47 g (91%). $^1$H NMR (CDCl$_3$); δ 7.2 (m, 15H); 5.0 (s, 1H); 3.6 (t, 6H); and 2.8 (t, 6H); $^{13}$C NMR (CDCl$_3$); δ 138.61, 128.81, 128.17, 126.10, 112.52, 64.76, and 35.89.

EXAMPLE 2

Preparation of tris(9-decenyl) orthoformate

The procedure described above is suitable for use in preparing tris(9-decenyl) orthoformate using 9-decen-1-ol (42.5g, Rosalva - IFF), and triethyl orthoformate (10 g), to yield 27 g (83%) of a clear oil isolated by Kugelrohr distillation within the range 140–150° C., at 0.1 mm Hg. $^1$H NMR (CDCl$_3$) δ 5.8 (m, 3H); 5.1 (s, 1H); 4.9 (m, 6H); 3.5 (t, 6H); 2.0 (m, 6H); 1.6 (m, 6H); and 1.35 (m, 30H); $^{13}$C NMR (CDCl$_3$) δ 138.87, 113.89, 112.47, 67.74, 33.56, 29.28, 29.19, 29.15, 28.84, 28.68, and 25.52

EXAMPLE 3

Preparation of tris(cis-3-hexenyl) orthoformate

The procedure described above is suitable for use in preparing tris(cis-3-hexenyl) orthoformate using cis-3-hexenol (115 g), and triethyl orthoformate (42.7 g) to yield 79 g (88%) of a clear oil isolated by Kugelrohr distillation at 100° C., 0.1 mm Hg. $^1$H NMR (CDCl$_3$) δ 5.45 (m, 3H); 5.35 (m, 3H); 5.2 (s, 1H); 3.5 (t, 6H); 2.35 (d,t, 6H); 2.05 (d,t, 6H), and 1.0 (t, 9H); $^{13}$C NMR (CDCl$_3$) δ 133.57, 124.46, 112.31, 63.51, 27.36, 20.39, and 13.99

EXAMPLE 4

Preparation of tris(geranyl/neryl)orthoformate

To a 500 mL single neck flask equipped with a short path distillation head and a magnetic stirrer is combined a mixture of geraniol and nerol (52 g, Bush Boake Allen 70/30), triethyl orthoformate (10 g) and anhydrous citric acid (0.66 g) under a nitrogen atmosphere. (The use of citric acid prevents undesired decomposition of the product). The reaction mixture is heated for 4 hr at 100° C. during which time ethanol is removed via distillation. The reaction progress is monitored by the amount of ethanol generated and by silica gel thin layer chromatography (TLC) eluting with 4% ethyl acetate/petroleum ether and development with iodine stain. Upon completion, the reaction mixture is diluted with diethyl ether (200 mL) and the organic phase washed three times with saturated aqueous sodium carbonate. The organic phase was dried over magnesium sulfate, filtered, and the resulting clear solution is concentrated in vacuo. The product is purified by Kugelrohr distillation wherein the fraction in the range 140–150° C., at 0.1 mm Hg is collected to yield 23.5 g (73%). $^1$H NMR (CDCl$_3$) δ 5.35 (m, 3H); 5.25 (m, 1H); 5.1 (m, 3H); 4.15 (m, 6H); 2.1 (m, 12H); and 1.8–1.6 (m, 27H); $^{13}$C NMR (CDCl$_3$) δ 139.96, 139.75, 131.53, 131.25, 123.73, 123.59, 120.97, 119.99, 111.01, 60.40, 60.05, 39.31, 31.97, 26.48, 26.12, 25.39, 23.19, 17.37, and 16.14.

EXAMPLE 5

Preparation of tris(phenylethyl) orthoacetate

To a 250 mL three neck flask equipped with a rubber septum fitted with a needle, a drying tube charged with Drierite, a stopper, and equipped with a magnetic stirrer, is added phenylethyl alcohol (100 g), trimethylorthoacetate (30 g) and 3 drops of concentrated sulfuric acid. Nitrogen is slowly bubbled through the solution over a 4 day period to remove the methanol which is produced. The mixture is then diluted in diethyl ether (300 mL) and washed three times with saturated aqueous sodium carbonate. The organic phase is dried over magnesium sulfate, filtered, and the resulting clear solution is concentrated. The product is purified by Kugelrohr distillation wherein the fraction in the range 150–170° C., at 0.1 mm Hg is collected to yield 23.5 g (74%). $^1$H NMR (CDCl$_3$) δ 7.2 (m, 15H); 3.6 (t, 6H); 2.8 (t, 6H); and 1.4 (s, 3H); $^{13}$C NMR(CDCl$_3$)δ 138.92, 128.93, 128.15, 126.07, 114.18, 63.01, 36.26, and 20.20.

EXAMPLE 6

Preparation of tris(cis-3-hexenyl) orthoacetate

The procedure described above is suitable for use in preparing tris(cis-3-hexenyl) orthoacetate using cis-3-hexenol (65 g) and trimethyl orthoacetate (22.2 g) and para-toluenesulfonic acid monohydrate (0.35 g) over 5 days, to yield 38.6g (64%) of a clear oil isolated by Kugelrohr distillation within the range 110–120° C., at 0.1 mm Hg. 1H NMR (CDCl$_3$) δ 5.3 (m, 6H), 3.4 (t, 6H), 2.25 (d,t, 6H); 2.0 (d,t, 6H); 1.4 (s, 3H); and 0.9 (t, 9H); $^{13}$C NMR (CDCl$_3$) δ 133.73, 125.03, 113.80, 61.48, 27.54, 20.29, 19.92, and 13.94.

EXAMPLE 7

Preparation of bis(geranyl/neryl) vanillin acetal

To a 1 L single-neck flask equipped with a Dean-Stark trap, condenser, and magnetic stirrer under a nitrogen atmosphere is added vanillin (60 g), geraniol/nerol (182 g, Bush Boake Allen 70/30), anhydrous citric acid (3.78 g) and 400 mL benzene. The mixture is refluxed for 24 hr during which time 4 mL of water is isolated in the Dean-Stark trap. The trap is replaced with a Soxhiet extractor having a cup containing 300 mL of activated molecular sieves (3 Å) and the reaction is refluxed for an addition 24 hr. The reaction mixture is cooled and washed four times with saturated aqueous sodium carbonate. The organic phase is dried over magnesium sulfate, filtered, and the resulting clear solution is concentrated in vacuo. The product is purified by Kugelrohr distillation wherein the fraction above 80° C., at 0.1 mm Hg is retained to yield 111 g (84%) of a yellow oil comprising three isomers. $^1$H NMR (CDCl$_3$) δ 7.1–6.9 (m, 3H); 5.75 (s,b, 1H); 5.5 (s, 1H); 5.35 (m, 2H); 5.10 (m, 2H); 4.1 (m, 4H), 3.85 (s, 3H); 2.1 (m, 8H); and 1.75–1.60 (ms, 18H); $^{13}$C NMR (CDCl$_3$) δ 146.25, 145.47, 140.21, 139.93, 131.63, 131.36, 130.93, 123.78, 123.63, 121.34, 120.39, 119.82, 113.64, 108.83, 100.04, 61.66, 61.55, 61.36, 55.66, 39.39, 32.04, 26.54, 26.17, 25.44, 23.28, 17.44, and 16.23.

EXAMPLE 8

Preparation of bis(phenylethyl) benzaldehyde acetal

To a 1 L single-neck flask equipped with a Dean-Stark trap, condenser, and magnetic stirrer under a nitrogen atmosphere is added benzaldehyde (31.5 g), phenylethyl alcohol (159.5 g), and para-toluenesulfonic acid monohydrate (1.46 g) and 320 mL toluene. The mixture is refluxed for 3 hr during which time 5 mL of water is isolated in the Dean-Stark trap and TLC analysis (4% ethyl acetate/petroleum ether as the eluent) indicates all of the benzaldehyde is consumed. Upon completion, the reaction mixture is diluted with diethyl ether (200 mL) and the organic phase washed three times with saturated aqueous sodium carbonate. The organic phase is dried over magnesium sulfate, filtered, and the resulting clear solution is concentrated in vacuo. The product is purified by Kugelrohr distillation wherein the fraction above 70° C., 0.3 mm Hg is retained and yields 58.6 g (59%) of a clear-yellow oil. The material obtained is further purified by chromatography over silica gel (Merck 230–400 mesh) eluting with 4% ethyl acetate/1% triethyl amine/petroleum ether to give a clear oil. $^1$H NMR (CDCl$_3$) δ 7.3 (m, 15H); 5.5 (s, 1H); 3.6 (t, 4H); and 2.8 (t, 4H). $^{13}$C NMR (CDCl$_3$) δ 139.07, 128.97, 128.27, 128.10, 126.70, 126.15, 101.44, 66.08, and 36.34.

EXAMPLE 9

Preparation of tetrakis(phenylethyl) orthocarbonate

To a 250 mL three neck flask equipped with a rubber septum fitted with a needle, a drying tube charged with Drierite, a stopper, and equipped with a magnetic stirrer, is added phenylethyl alcohol (36.7 g), tretraethylorthocarbonate (9.84 g) and para-toluenesulfonic acid monohydrate (0.21 g). Nitrogen is slowly bubbled through the solution while stirring over 36 hr to remove the ethanol which is produced. The mixture is then diluted with diethyl ether (300 mL) and washed three times with saturated aqueous sodium carbonate. The organic phase is dried over magnesium sulfate, filtered, and concentrated. The product is purified by Kugelrohr distillation wherein the fraction above 100° C., 0.1 mm Hg is retained to yield 12.8 g (50%) of a clear oil. $^1$H NMR (CDCl$_3$) δ 7.2 (m, 16H); 3.6 (t, 8H); and 2.8 (t, 8H); $^{13}$C NMR (CDCl$_3$) δ 138.84, 128.89, 128.11, 126.03, 119.57, 63.75, and 35.8.

In addition to the above procedure of Example 9, suitable methods for preparing the orthocarbonate pro-fragrances of the present invention can be found in "Synthesis of Carboxylic and Carbonic Orthoesters", R. H. DeWolfe, Synthesis, pg. 153, (1974) and "Synthesis of Aryl Carbonates", N. Narasimhamurthy and A. G. Samuelson, Tetrahedron Letters, vol. 27, pg., 991, (1986) both incorporated herein by reference.

EXAMPLES 10–12

A deodorant gel stick of the present invention having the composition given below, and being essentially free of water, is prepared as follows.

TABLE II

| Ingredients | Weight % | | |
|---|---|---|---|
| | 10 | 11 | 12 |
| Dipropylene glycol | 39.85 | 51.95 | 75.10 |
| Sodium Stearate | 5.50 | 5.50 | 5.50 |
| PPG-3 myristyl ether | 29.40 | 25.33 | 15.00 |
| Cyclomethicone-D5 | 21.00 | 13.33 | — |
| Ethanol (absolute; 200 proof) | 1.80 | 1.44 | 1.95 |
| Zinc pyrithione[1] | 0.05 | 0.05 | 0.05 |
| Fragrance pro-accord[2] | 2.40 | 2.40 | 2.40 |

[1]Powder form commercially available from Olin.
[2]Fragrance pro-accord admixture comprising 75% tris(phenylethyl) orthoacetate and 25% tris(cis-3-hexenyl) orthoacetate All of the above materials, except the fragrance pro-accord, are vigorously mixed and heated to about 121° C. until the mixture is clear. The mixture is them cooled to about 80° C. and the pro-accord is added with stirring. The mixture is poured into stick molds and cooled to room temperature forming the deodorant gel stick compositions of the present invention.

EXAMPLES 13–16

A personnel cleanser composition is prepared by combining the following ingredients using conventional mixing techniques.

TABLE III

| Ingredients | Weight % | | | |
|---|---|---|---|---|
| | 13 | 14 | 15 | 16 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer[1] | 0.150 | 0.150 | 0.150 | 0.150 |
| Carbomer 954[2] | 0.250 | 0.250 | 0.250 | 0.250 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide[3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil[4] | — | 5.00 | — | — |
| Phase E | | | | |
| Phenoxyethanol | 0.5 | 0.5 | — | 0.5 |

TABLE III-continued

| Ingredients | Weight % | | | |
|---|---|---|---|---|
| | 13 | 14 | 15 | 16 |
| Pro-accord[5] | 1.5 | 1.5 | — | — |
| Pro-accord[6] | — | — | 2.20 | 1.5 |
| Phase F | | | | |
| Glucose amide | 0.96 | 0.96 | 0.96 | 0.96 |

[1]Available as Pemulen ® from B.F. Goodrich Corporation.
[2]Available as Carbomer ® 954 from B.F. Goodrich Corporation.
[3]As a 50% aqueous solution.
[4]Light mineral oil available as Drakeol 5 from Penreco, Dickenson, TX.
[5]Fragrance pro-accord tris(cis-3-hexenyl) orthoformate
[6]Fragrance pro-accord admixture comprising 75% tris(phenylethyl) orthoacetate and 25% tris(cis-3-hexenyl) orthoformate The above Examples 13–16 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

What is claimed is:

1. A composition applied to skin having increased fragrance retention and fragrance longevity, comprising:
   a) at least about 0.01% by weight, of a fragrance delivery system comprising one or more pro-accords, provided each pro-accord:
      i) is formed from n number of fragrance raw materials;
      ii) contains n number of fragrance raw materials wherein n is an integer from 1 to 3 in a releasable form;
      iii) releases at least n+1 fragrance raw materials;
      iv) comprises fragrance raw materials having a molecular weight greater than or equal to about 100 g/mol;
      v) has a molecular weight greater than or equal to about 300 g/mol;
      vi) has a molecular weight at least two times greater than the lowest molecular weight fragrance raw material which comprises said pro-accord; and
      vii) has a fragrance release half-life of greater than or equal to 0.1 hours at pH 5.3 and less than or equal to about 12 hours at pH 2.5 when measured in $NaH_2PO_4$ buffer;
   b) at least about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, and mixtures thereof; and
   c) the balance carriers.

2. A composition according to claim 1 wherein said pro-accord has an odor value greater than or equal to 1 and a molecular weight greater than or equal to 300 g/mol.

3. A composition applied to skin having increased fragrance retention and fragrance longevity, comprising:
   a) at least about 0.01% by weight, of a fragrance delivery system comprising one or more pro-accords, provided at least one pro-accord:

i) comprises fragrance raw materials having a molecular weight greater than or equal to about 100 g/mol;
ii) has a molecular weight greater than or equal to about 300 g/mol;
iii) has a molecular weight at least two times greater than the lowest molecular weight fragrance raw material which comprises said pro-accord; and
iv) has a fragrance release half-life of greater than or equal to 0.1 hours at pH 5.3 and less than or equal to about 12 hours at pH 2.5 when measured in $NaH_2PO_4$ buffer b) at least about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, and mixtures thereof; and c) the balance carriers.

4. A composition according to claim 3 wherein said pro-accord is selected from the group consisting of acetals, ketals, orthoesters, orthocarbonates, and mixtures thereof.

5. A composition according to claim 3 wherein said pro-accord releases a binary accord.

6. A composition according to claim 4 wherein said pro-accord has the formula:

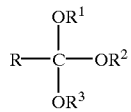

wherein R is hydrogen, $C_1$–$C_8$ linear alkyl, $C_3$–$C_{20}$ branched alkyl, $C_3$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$, $R^2$ and $R^3$ are independently $C_1$–$C_{20}$ linear, branched, or substituted alkyl; $C_2$–$C_{20}$ linear, branched, or substituted alkenyl; $C_3$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl, and mixtures thereof.

7. A composition according to claim 6 wherein said pro-accord compound releases a fragrance raw material alcohol selected from the group consisting of 4-(1-methylethyl)cyclohexanemethanol, 2,4-dimethyl-3-cyclohexen-1-ylmethanol, (2,4-dimethylcyclohex-1-yl)methanol, (2,4,6-trimethyl-3-cyclohexen-1-yl)methanol, 2-phenylethanol, 1-(4-isopropylcyclohexyl)-ethanol, 2,2-dimethyl-3-(3-methylphenyl)propan-1 -ol, 3-phenyl-2-propen-1-ol, 2-methyl- 4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 4-methyl-3-decen-5-ol, benzyl alcohol, 2-methoxy-4-(1-propenyl)phenol, 2-methoxy-4-(2-propenyl)phenol, and mixtures thereof.

8. A composition according to claim 6 wherein said pro-accord compound releases a fragrance raw material ester having the formula:

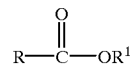

wherein R is hydrogen, methyl, ethyl, phenyl, and mixtures thereof; $R^1$ is selected from the group consisting of 4-(1-methylethyl)cyclohexanemethyl, 2,4-dimethyl-3-cyclohexen- 1-ylmethyl, 2,4-dimethylcyclohex-1-ylmethyl, 2,4,6-trimethyl-3-cyclohexen-1-ylmethyl, 2-phenylethyl, 1-(4-isopropylcyclo-hexyl)ethyl, 2,2-dimethyl-3-(3-methylphenyl)propan-1-yl, 3-phenyl-2-propen-1-yl , 2-methyl-4-(2,2,3-trimethyl-3-cyclopenten-1-yl)-2-buten-1-yl, 3-methyl-5-phenylpentan-1-yl, 3-methyl-5-(2,2,3-trimethyl-3-cyclopenten-1-yl)-4-penten-2-yl, 2-methyl-4-phenylpentan-1-yl, cis-3-hexen-1-yl, 3,7-dimethyl-6-octen-1-yl, 3,7-dimethyl-2,6-octadien-1-yl, 7-methoxy-3,7-dimethyloctan-2-yl, 6,8-dimethylnonan-2-yl, cis-6-nonen-1-yl, 2,6-nonadien-1-yl, 4-methyl-3-decen-5-yl, benzyl, 2-methoxy-4-(1-propenyl)phenyl, 2-methoxy-4-(2-propenyl)phenyl, and mixtures thereof.

9. A composition according to claim 4 wherein said pro-accord is an acetal or a ketal having the formula:

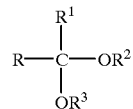

wherein R is $C_1$–$C_{20}$ linear alkyl, $C_3$–$C_{20}$ branched alkyl, $C_3$–$C_{20}$ cyclic alkyl, $C_6$–$C_{20}$ branched cyclic alkyl, $C_2$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof, $R^1$ is hydrogen or R; $R^2$ and $R^3$ are each independently selected from the group consisting of $C_1$–$C_{20}$ linear alkyl, $C_3$–$C_{20}$ branched alkyl, $C_6$–$C_{20}$ cyclic alkyl, $C_6$–$C_{20}$ branched cyclic alkyl, $C_2$–$C_{20}$ linear alkenyl, $C_3$–$C_{20}$ branched alkenyl, $C_6$–$C_{20}$ cyclic alkenyl, $C_6$–$C_{20}$ branched cyclic alkenyl, $C_6$–$C_{20}$ aryl, $C_7$–$C_{20}$ substituted aryl, and mixtures thereof.

10. A composition according to claim 9 wherein said pro-accord compound releases a fragrance raw material aldehyde selected from the group consisting of 4-(4-hydroxy-4-methylpentyl)-3-cyclohexene-1-carboxaldehyde, phenylacetaldehyde, methylnonyl acetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methyl-propanal, 3-(3,4-methylenedioxyphenyl)-2-methylpropan-1-al, 3-(4-ethylphenyl)-2,2-dimethylpropanal, 3-(3-isopropylphenyl)butan-1-al, 2,6-dimethylhep-5-en-1-al, n-decanal, n-undecanal, n-dodecanal, 3,7-dimethyl-2,6-octadien-1-al, 4-methoxybenzaldehyde, 3-methoxy-4-hydroxybenzaldehyde, 3-ethoxy-4-hydroxybenzaldehyde, 3,4-methylenedioxy-benzaldehyde, 3,4-dimethoxybenzaldehyde, and mixtures thereof.

11. A composition according to claim 9 wherein said pro-accord compound releases a fragrance raw material alcohol selected from the group consisting of 4-(1-methylethyl)cyclohexanemethanol, 2,4-dimethyl-3-cyclohexen-1-ylmethanol, (2,4-dimethylcyclohex-1-yl) methanol, (2,4,6-trimethyl-3-cyclohexen-1-yl)methanol, 2-phenylethanol, 1-(4-isopropylcyclohexyl)-ethanol, 2,2-dimethyl-3-(3-methylphenyl)propan-1-ol, 3-phenyl-2- propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 9-decen-1-ol, 4-methyl-3-decen-5-ol, benzyl alcohol, 2-methoxy-4-(1-propenyl)phenol, 2-methoxy-4-(2-propenyl)phenol, and mixtures thereof.

12. A composition according to claim 9 wherein said pro-accord compound releases a fragrance raw material ketone selected from the group consisting of α-damascone, β-damascone, δ-damascone, β-damascenone, muscone, 6,7-dihydro-1,1,2,3,3-pentamethyl-4(5H)-indanone, cis-jasmone, dihydro-jasmone, α-ionone, β-ionone, dihydro-β-ionone, γ-methyl ionone, α-iso-methyl ionone, 4-(3,4-methylenedioxyphenyl)butan-2-one, 4-(4-hydroxy-phenyl)butan-2-one, methyl β-naphthyl ketone, methyl cedryl ketone, 6-acetyl-1,1,2,4,4,7-hexamethyltetralin, 1-carvone, 5-cyclohexadecen-1-one, and mixture thereof.

13. A composition according to claim 12 wherein said pro-accord compound releases a fragrance raw material alcohol selected from the group consisting of 4-(1-methylethyl)cyclohexanemethanol, 2,4-dimethyl-3-cyclohexen-1-ylmethanol, (2,4-dimethylcyclohex-1-yl)methanol, (2,4,6-trimethyl-3-cyclohexen-1-yl)methanol, 2-phenylethanol, 1-(4-isopropylcyclohexyl)-ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 9-decen-1-ol, 4-methyl-3-decen-5-ol, benzyl alcohol, 2-methoxy-4-(1-propenyl)phenol, 2-methoxy-4-(2-propenyl)phenol, and mixtures thereof.

14. A composition according to claim 4 wherein said pro-accord has the formula:

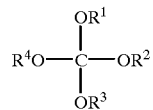

wherein $R^1$, $R^2$, $R^3$, and $R^4$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy: $C_6$–$C_{40}$ substituted or unsubstituted alkyleneoxyaryl; $C_6$–$C_{40}$ oxyalkylenearyl; and mixtures thereof.

15. A composition according to claim 14 wherein said pro-accord compound releases a fragrance raw material alcohol selected from the group consisting of 4-(1-methylethyl)cyclohexanemethanol, 2,4-dimethyl-3-cyclohexen-1-ylmethanol, (2,4-dimethylcyclohex-1-yl)methanol, (2,4,6-trimethyl-3-cyclohexen-1-yl)methanol, 2-phenylethanol, 1-(4-isopropylcyclohexyl)-ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 9-decen-1-ol, 4-methyl-3-decen-5-ol, benzyl alcohol, 2-methoxy-4-(1-propenyl)phenol, 2-methoxy-4-(2-propenyl)phenol, and mixtures thereof.

* * * * *

UNITED STATES PATENT AND TRADEMARK OFFICE
CERTIFICATE OF CORRECTION

PATENT NO. : 6,087,322
DATED : July 11, 2000
INVENTOR(S) : Joseph Paul Morelli et al.

It is certified that error appears in the above-identified patent and that said Letters Patent is hereby corrected as shown below:

Column 36,
Line 39, claim 1, sub-paragraph a) ii) should read -- contains $n$ number of fragrance raw materials in a releasable form; --
Line 42, claim 1, sub-paragraph a) iv) should read -- comprises fragrance raw materials wherein n is an integer from 1 to 3 having a molecular weight greater than or equal to about 100 g/mol; --

Signed and Sealed this

Twenty-fifth Day of September, 2001

Attest:

NICHOLAS P. GODICI
Attesting Officer    Acting Director of the United States Patent and Trademark Office